(12) United States Patent
Bakaletz et al.

(10) Patent No.: US 7,229,622 B2
(45) Date of Patent: Jun. 12, 2007

(54) SYNTHETIC CHIMERIC FIMBRIN PEPTIDES

(75) Inventors: Lauren O. Bakaletz, Columbus, OH (US); Pravin T. P. Kaumaya, Westerville, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 621 days.

(21) Appl. No.: 10/223,711

(22) Filed: Aug. 19, 2002

(65) Prior Publication Data
US 2003/0113344 A1 Jun. 19, 2003

Related U.S. Application Data

(60) Division of application No. 09/148,711, filed on Sep. 4, 1998, now Pat. No. 6,436,405, which is a continuation of application No. 08/460,502, filed on Jun. 2, 1995, now Pat. No. 5,843,464.

(51) Int. Cl.
  *A61K 39/02* (2006.01)

(52) U.S. Cl. ............................. 424/190.1; 424/192.1; 424/197.11

(58) Field of Classification Search .................. 514/2; 424/256.1
See application file for complete search history.

(56) References Cited

U.S. PATENT DOCUMENTS

| | | | |
|---|---|---|---|
| 5,110,908 A | | 5/1992 | Deich et al. |
| 5,766,608 A | * | 6/1998 | Kolattukudy et al. ..... 424/256.1 |
| 5,843,464 A | * | 12/1998 | Bakaletz et al. ......... 424/256.1 |
| 6,436,405 B1 | | 8/2002 | Bakaletz et al. |

FOREIGN PATENT DOCUMENTS

WO 94/26304 11/1994

OTHER PUBLICATIONS

Sambrook et al (Molecular Cloning A Laboratory Manual, second edition), Cold Spring Harbor Laboratory Press, 1989, , vol. 3, chapter 17, pp. 17.1-17.44.*
Rudinger et al, in "Peptide Hormones", edited by Parsons, J.A., University Park Press, Jun. 1976, p. 6 (of record in IDS).*
Burgess et al., The Journal of Cell Biology, 111:2129-2138, 1990 (of record in IDS).*
Lazar et al., Molecular and Cellular Biology, 8(3):1247-1252, 1988 (of record in IDS).*
Jobling et al. (Mol. Microbiol., 1991, 5(7):1755-67( of record in IDS).*
"Possible Dissociation of the Heparin-binding and Mitogenic Activities of Heparin-binding (Acidic Fibroblast) Growth Factor-2 from Its Receptor-binding Activities by Site-Directed Mutagenesis of a Single Lysine Residue" by Burgess, et al., *The Journal of Cell Biology*, vol. 111, 1990, pp. 2129-2138.

"Analysis of structure and function of the B subunit of cholera toxin by the use of site-directed mutagenesis" by Jobling, et al., *Molecular Microbiology*, (1991)5(7) pp. 1755-1767.
"Characteristics of the amino acids as components of a peptide hormone sequence" by Rudinger, et al., *Peptide Hormones* Parson, J.A. editor, Baltimore University Park Press, 1976, pp. 1-6.
"Transforming Growth Factor α: Mutation of Aspartic Acid 47 and Leucine 48 Results in Different Biological Activities" by Lazar, et al., *Molecular and Cellular Biology*, vol. 8, No. 3, Mar. 1998, pp. 1247-1252.
Abstract B-131 "Protection Against Histopathological Changes of Tympanic Membrane (TM) and Middle Ear Mucosa (MM) in a Chinchilla Model of Otitis Media by Immunization with Fimbrial Protein Isolated From Nontypable *Haemophilus influenza* (NTHi) Strain #1128" by Bakaletz, et al., American Society for Microbiology, 93rd General Meeting, May 16-20, 1993, Atlanta, Georgia.
Abstract, "The Effect of Immunizations with Fimbrial Protein in a Chinchilla Model of Nontypable *Haemophilus influenzae*-Induced Experimental Otitis Media" by Bakaletz, et al., Second Extraordinary International Symposium on Recent Advances in Otitis Media, Mar. 31-Apr. 3, 1993, Oita, Japan.
Abstract, "An Investigation of the Molecular Basis of the Adherence of Nontypable *Haemophilus influenzae* to Mucosal Epithelium" by Bakaletz, et al., Molecular Biology of Hearing and Deafness Conference, LaJalla, California, May 1-4, 1992.
Abstract B-169, "Passive Immunization of Chinchillas with Anti-NTHi Fimbrial Serum and Protection Against Experimental Otitis Media" by Bakaletz, et al. Fifth International Symposium, Recent Advances in Otitis Media, May 20-24, 1991, Columbus, Ohio.
Abstract, "Serological Relatedness of Fimbriae Expressed by NTHi Isolates Recovered from Children with Chronic Otitis Media" by Bakaletz, et al., Fifth International Symposium, Recent Advances in Otitis Media, May 20-24, 1991, Columbus, Ohio.

(Continued)

*Primary Examiner*—Patricia A. Duffy
(74) *Attorney, Agent, or Firm*—Calfee, Halter & Griswold LLP

(57) ABSTRACT

The present invention provides synthetic chimeric fimbrin peptides which induce an immunogenic response in animals to non-typable *Haemophilus influenzae* and that do not require tedious purification techniques. The synthetic chimeric fimbrin peptides reduce the severity of otitis media caused by *Haemophilus influenzae*. The synthetic chimeric fimbrin peptides are synthesized using commercially available peptide synthesizers. The synthetic chimeric fimbrin peptides comprises three peptide units. The first peptide unit is a subunit of the fimbrin protein. Preferably, the fimbrin subunit is comprised of the amino acids of Sequence ID No. 1 or Sequence ID No. 2. The second peptide unit is a t cell epitope, and preferably has the amino acid sequence of SEQ ID NO. 3. The third peptide unit is a linker peptide unit which joins the first and second peptide unit. The linking sequence preferably has from about 2 to about 15 amino acids, more preferably from about 2 to about 10 amino acids, most preferably from about 5 to about 6 amino acids. The synthetic chimeric fimbrin peptides are useful immunognes against NTHi and also useful as laboratory tool for detecting antibodies in sera. The invention also relates to an immunogenic composition containing the synthetic chimeric fimbrin peptides and a pharmacologically acceptable carrier.

8 Claims, 5 Drawing Sheets

OTHER PUBLICATIONS

Abstract, "Isotype Specific Antibody Response Against OMPs and Fimbriae of Nontypable *Haemphilus influenzae* Isolated From Patients with Chronic Otitis Media" by DeMaria, et al., Fifth International Symposium, Recent Advances in Otitis Media, May 20-24, 1991, Columbus, Ohio.

Abstract, "Immunological Responsiveness of Chincillas to Isolated Fimbrial Proteins of Nontypable *Hemophilus influenzae* During Experimental Otitis Media" by Bakaletz, et al., Eleventh Midwinter Research Meeting, Association for Research in Otolaryngology, Jan. 31-Feb. 4, 1988, Clearwater Beach, Florida.

Abstract, "Inhibition of Adherence of Nontypable *Haemophilus influenzae* to Human Oropharyngeal Cells" by Bakaletz, et al., Twelfth Midwinter Research Meeting, Association for Research in Otolaryngology, Feb. 5-9, 1989, St. Petersburg Beach, Florida.

Abstract, "Role of Degree of Fimbriation on Ability of Nontypable *Haemophilus influenzae* to Colonize The Nasopharynx and Middle Ears of the Chinchilla" by Bakaletz, et al., Thirteenth Midwinter Research Meeting, Association for Research in Otolaryngology, Feb. 4-8, 1990, St. Petersburg Beach, Florida.

Abstract, Chinchilla Immunological Responsiveness to Isolated Outer Membrane and Fimbrial Proteins Of Nontypable *Haemophilus influenzae*, by Bakaletz, et al., Thirteenth Midwinter Research Meeting, Association for Research in Otolaryngology, Feb. 4-8, 1990, St. Petersburg Beach, Florida.

Abstract B-66, Colonization of the Chinchilla Middle Ear and Nasopharynx by Fimbriated Isolates of Nontypable *Haemophilus influenzae*, by Bakaletz, et al., 90th Annual Meeting of the American Society for Microbiology, May 13-17, 1990, Anaheim, California.

Abstract, "Presumptive Identification of the NTHi Adhesin for Human Oropharnygeal and Chinchilla Middle Ear Epithelial Cells" by Bakaletz, et al., Fifth International Symposium, Recent Advances in Otitis Media, May 20-24, 1991, Columbus, Ohio.

Abstract, "Inhibition of Adherence of NTHi to Human Oropharyngeal Cells—An ELISA Essay" by Bakaletz, et al., Fifth International Symposium, Recent Advances in Otitis Media, May 20-24, 1991, Columbus, Ohio.

Abstract, "Cloning and Sequencing of a Pilin Gene from NTHi Strain #1128" by Bakaletz, et al., Fifth International Symposium, Recent Advances in Otitis Media, May 20-24, 1991, Columbus, Ohio.

Abstract, "Protection of Chinchillas Against Experimental Otitis Media via Active Immunization with NTHi Strain #1128 Fimbrin" by Bakaletz, et al., Fifteenth Midwinter Research Meeting, Association for Research in Otolaryngology, Feb. 2-6, 1992, St. Petersburg Beach, Florida.

"Frequency of Fimbriate Isolates of Nontypable *Haemophilus influenzae* from the Middle Ears and Nasopharynges of Patients with Chronic Otitis Meda" by Bakaletz, et al., Proceedings of the Fourth International Symposium, Recent Advances in Otitis Media, Jun. 1987, Columbus, Ohio, pp. 331-335.

"Evalution of pilus vaccines for prevention of experimental otitis media caused by nontypable *Haemophilus influenzae*" by Karasic, et al., *Pediatr Ifect Dis J*, vol. 8, No. 1, 1989, pp. S62-S65.

"Cloning and Expression in *Escherichia coli* of LKP Pilus Genes from a Nontypeable *Haemophilus influenzae* Strain" by Kar, et al., *Infection and Immunity*, vol. 58, No. 4, Apr. 1990, pp. 903-908.

"Design and Development of pilus vaccines for *Haemophilus influenzae* diseases" by Brinton, et al., *Pediatr Infect Dis J*, vol. 8, No. 1, 1989, p. S54-S61.

Abstract, "Passive immunization of chinchillas against experimental otitis media with anti-NTHi fimbrial subunit (fimbrin) sera" by Bakaletz, et al., 91st General Meeting of the American Society for Microbiology, May 5-9, 1991, Dallas, Texas.

"Somatic antigens of *Haemophilus influenzae* as vaccine components" by Murphy, et al., *Pediatr Infect Dis J*, vol. 8, No. 1, 1989, pp. S66-S68.

"Loss of Capsule Expression by *Haemophilus influenzae* Type b Results in Enhanced Adheerence to and Invasion of Human Cells" by Geme, et al., *Infection and Immunity*, vol. 59, No. 4, Apr. 1991, pp. 1325-1333.

"*Haemophilus influenzae* Adheres to and Enters Cultured Human Epithelial Cells" by Geme, et al., *Infection and Immunity*, vol. 58, No. 12, Dec. 1990, pp. 4036-4044.

"Comparison of Hemagglutinating Pili of *Haemophilus influenzae* Type b with Similar Structures of Nontypeable *H. influenzae*" by Gilsdorf, et al., *Infection and Immunity*, vol. 60, No. 2, Feb. 1992, pp. 374-379.

"Cloning and expression in *Escherichia coli* of *Haemophilus influenzae* fimbrial genes establishes adherence to oropharyngeal epithelial cells" by van Ham, et al., *The EMBO Journal*, vol. 8, No. 11, 1989, pp. 3535-3540.

"Effect of Pili-Specific Antibodies on the Adherence of *Haemophilus influenzae* Type b to Human Buccal Cells" by Forney,e tal., *The Journal of Infectious Diseases*, 1992:165:464-470.

"Inability to Express Fimbriae Results in Impaired Ability of *Haemophilus influenzae* b to Colonize the Nasopharynx" by Weber, et al., *Infection and Immunity*, vol. 59, No. 2, Dec. 1991, pp. 4724-4728.

"Interaction of Nontypable *Haemophilus influenzae* with Human Repiratory Mucosa In Vitro" by Read, et al., *The Journal of Infectious Diseases*, 1991:163:549-558.

"Characterization of Antigens from Nontypable *Haemophilus influenzae* Recognized by Human Bactericidal Antibodies" by Gnhem, et al., *J. Clin. Invest.*, vol. 75, May 1985, pp. 1645-1658.

"Modification of Otitis Media in Chinchillas Rechallenged with Nontypable *Haemophilus influenzae* and Serological Response to Outer Membrane Antigens" by Karasic, et al., *The Journal of Infectious Diseases*, vol. 151, No. 2, Feb. 1985, pp. 273-279.

"Development of serum bactericidal activity following nontypable *Haemophilus influenzae* acute otitis media" by Barenkamp, et al., *Pediatr Infect Dis J*, vol. 9, No. 5, 1990, pp. 333-339.

"Protection of Serum Antibodies in Experimental Nontypable *Haemophilus influenzae* Otitis media" by Barenkamp, et al., *Infection and Immunity*, vol. 52, No. 2, May 1986, pp. 572-578.

"Nontypable *Haemophilus influenzae*: A Review of Clinical Aspects, Surface Antigens, and the Human Immune Response to Infection" by Murphy, et al., *Review of Infectious Diseases*, vol. 9, No. 1, Jan.-Feb. 1987, pp. 1-13.

"Comparison and Analysis of the Nucleotide Sequences of Pilin Genes from *Haemophilus influenzae* Type b Strains Eagan and M43" by Forney, et al., *Infection and Immunity*, vol. 59, No. 6, Jun. 1991, pp. 1991-1996.

"Purification and Partial Characterization of Outer Membrane Proteins P5 and P6 from *Haemophilus influenzae* Type b" by Munson, et al., *Infection and Immunity*, vol. 49, No. 3, Sep. 1985, pp. 544-549.

"Evaluation of Mixtures of Purified *Haemophilus influenzae* Outer Membrane Proteins in Protection Against Challenge with Nontypable *H. influenzae* in the Chinchilla Otitis Media Model" by Green, et al., *Infection and Immunity*, vol. 61, No. 5, May 1993, pp. 1950-1957.

"The *e* (P4) Outer Membrane Protein of *Haemophilus influenzae*: Biologic Activity of Anti-*e* Serum and Cloning and Sequencing of the Structural Gene" by Green, et al., *Infection and Immunity*, vol. 59, No. 9, Sep. 1991, pp. 3191-3198.

"Frequency and Fimbriation of Nontypable *Haemophilus influenzae* and Its Ability to Adhere to Chinchilla and Human Respiratory Epithelium" by Bakaletz, et al., *Infection and Immunity*, vol. 56, No. 2, Feb. 1998, pp. 331-335.

"Immunological Responsiveness of Chinchillas to Outer Membrane and Isolated Fimbrial Proteins of Nontypable *Haemophilus influenzae*" by Bakaletz, et al., *Infection and Immunity*, vol. 57, No. 10, Oct. 1989, pp. 3226-3229.

"Serum and Middle Ear Antibody Response in the Chinchilla during Otitis Media with Effusion Induced by Nonviable Nontypable *Haemophilus influenzae*" by DeMaria, et al., *The Journal of Infectious Diseases*, 1992:165(suppl 1):S196-197.

Abstract P696, "Positioning of Promiscuous T Cell Epitopes on a Single Matrix, Multicomponent Combination Vaccine in Elucidation of MHC-Unrestricted Responses" by Woodbine, et al., Fourteenth American Peptide Symposium, Jun. 18-23, 1995, Columbus, Ohio.

Abstract, "Use of Synthetic Peptides of Fimbrin Isolated from NTHi Strain #1128 as Immunogens in Rabbits and Chinchillas" by Bakaletz, et al., Sixth International Symposium, Recent Advances in Otitis Media, Jun. 4O8, 1995, Fort Lauderdale, Florida.

Abstract S9, "Immunological aspects of otitis media" by Bakaletz, et al., Sixth International Congress Pediatric Otorhinolaryngology, May 29-Jun.1, 1994, Rotterdam.

"Modeling Adenovirus Type 1-Induced Otitis Media in the Chinchilla: Effect on Ciliary Activity and Fluid Transport Function of Eustachian Tube Mucosal Epithelium" by Bakaletz, et al., *The Journal of Infectious Diseases*, 1993:168:865-72.

"Synergistic Effect of Adenovirus Type 1 and Nontypeable *Haemophilus influenzae* in a Chinchilla Model of Experimental Otitis Media" by Suzuki, et al., *Infection and Immunity*, vol. 62, No. 5, May 1994, pp. 1710-1718.

"De Novo Engineering of Peptide Immunogenic and Antigenic Determinants as Potential Vaccines" by Kaumaya, et al, *Peptides: Design, Synthesis and Biological Activity*, 1994, pp. 133-164.

"Molecular Cloning and Sequence of the Gene for Outer Membrane Protein P5 of *Haemophilus influenzae*" by Munson, et al., *Infection and Immunity*, vol. 61, No. 9, Sep. 1993, pp. 4017-4020.

"Chapter 100: Measles" by C. Sullivan, et al., *Infectious Disease, Fifth Edition*, J.B. Lippincott Company, Philadelphia 1994, pp. 892-902.

* cited by examiner

SEQUENCE LISTING

<160> NUMBER OF SEQ ID NOS: 12

<210> SEQ ID NO 1
<211> LENGTH: 18
<212> TYPE: PRT
<213> ORGANISM: Haemophilus influenzae

```
<400> SEQUENCE: 1

Arg Ser Asp Tyr Lys Phe Tyr Glu Asp Leu Asn Gly Thr Arg Asn His
1               5                   10                  15
Lys Lys

<210> SEQ ID NO 2
<211> LENGTH: 18
<212> TYPE: PRT
<213> ORGANISM: Haemophilus influenzae

<400> SEQUENCE: 2

Tyr Gln Trp Leu Thr Arg Val Gly Lys Tyr Arg Pro Gln Asp Lys Pro
1               5                   10                  15
Asn Thr

<210> SEQ ID NO 3
<211> LENGTH: 16
<212> TYPE: PRT
<213> ORGANISM: Measles virus

<400> SEQUENCE: 3

Leu Ser Leu Ile Lys Gly Val Ile Val His Arg Leu Glu Gly Val Glu
1               5                   10                  15

<210> SEQ ID NO 4
<211> LENGTH: 6
<212> TYPE: PRT
<213> ORGANISM: Artificial
<220> FEATURE:
<223> OTHER INFORMATION: synthetic construct

<400> SEQUENCE: 4

Gly Pro Ser Leu Lys Leu
1               5

<210> SEQ ID NO 5
<211> LENGTH: 19
<212> TYPE: PRT
<213> ORGANISM: Clostridium tetani

<400> SEQUENCE: 5

Asn Ser Val Asp Asp Ala Leu Ile Asn Ser Thr Ile Tyr Ser Tyr Phe
1               5                   10                  15
Pro Ser Val

<210> SEQ ID NO 6
<211> LENGTH: 17
<212> TYPE: PRT
<213> ORGANISM: Clostridium tetani

<400> SEQUENCE: 6

Pro Gly Ile Asn Gly Lys Ala Ile His Leu Val Asn Asn Gln Ser Ser
1               5                   10                  15
Glu

<210> SEQ ID NO 7
<211> LENGTH: 15
<212> TYPE: PRT
<213> ORGANISM: Clostridium tetani

<400> SEQUENCE: 7
```

Gln Tyr Ile Lys Ala Asn Ser Lys Phe Ile Gly Ile Thr Glu Leu
1               5                   10                  15

<210> SEQ ID NO 8
<211> LENGTH: 21
<212> TYPE: PRT
<213> ORGANISM: Clostridium tetani

<400> SEQUENCE: 8

Phe Asn Asn Phe Thr Val Ser Phe Trp Leu Arg Val Pro Lys Val Ser
1               5                   10                  15

Ala Ser His Leu Glu
            20

<210> SEQ ID NO 9
<211> LENGTH: 15
<212> TYPE: PRT
<213> ORGANISM: Hepatitis B virus

<400> SEQUENCE: 9

Phe Phe Leu Leu Thr Arg Ile Leu Thr Ile Pro Gln Ser Leu Asn
1               5                   10                  15

<210> SEQ ID NO 10
<211> LENGTH: 40
<212> TYPE: PRT
<213> ORGANISM: Artificial
<220> FEATURE:
<223> OTHER INFORMATION: synthetic construct

<400> SEQUENCE: 10

Arg Ser Asp Tyr Lys Phe Tyr Glu Asp Ala Asn Gly Thr Arg Asp His
1               5                   10                  15

Lys Lys Gly Pro Ser Leu Lys Leu Leu Ser Leu Ile Lys Gly Val Ile
            20                  25                  30

Val His Arg Leu Glu Gly Val Glu
        35                  40

<210> SEQ ID NO 11
<211> LENGTH: 40
<212> TYPE: PRT
<213> ORGANISM: Artificial
<220> FEATURE:
<223> OTHER INFORMATION: synthetic construct

<400> SEQUENCE: 11

Tyr Gln Trp Leu Thr Arg Val Gly Lys Tyr Arg Pro Gln Asp Lys Pro
1               5                   10                  15

Asn Thr Gly Pro Ser Leu Lys Leu Leu Ser Leu Ile Lys Gly Val Ile
            20                  25                  30

Val His Arg Leu Glu Gly Val Gly
        35                  40

<210> SEQ ID NO 12
<211> LENGTH: 20
<212> TYPE: PRT
<213> ORGANISM: Plasmodium falciparum

<400> SEQUENCE: 12

Thr Cys Gly Val Gly Val Arg Val Arg Ser Arg Val Asn Ala Ala Asn
1               5                   10                  15

```
Lys Lys Pro Glu
            20
```

SYNTHETIC CHIMERIC FIMBRIN PEPTIDES

CROSS REFERENCE TO RELATED APPLICATIONS

This application is a divisional application of U.S. patent Ser. No. 09/148,711, filed Sep. 4, 1998, now U.S. Pat. No. 6,436,405; which is a continuation of U.S. patent Ser. No. 08/460,502 filed Jun. 2, 1995, now U.S. Pat. No. 5,843,464.

BACKGROUND OF THE INVENTION

Otitis media is an infection of the middle ear that occurs primarily in children. Left untreated, the disease can result in hearing loss and developmental delays. It is estimated that otitis media accounted for 31 million of the 130 million office visits for respiratory diseases in the period from 1977–87. Recent data indicate that suppurative and unspecified otitis media rank first in the list of the 30 most common diagnoses requiring a physician's office visit for patients up to age 24. Over one billion dollars per year is spent on treatment of this disease and the related loss of income for working parents is estimated to be between $300 and $600 million. Approximately 83% of all children will have had at least one episode of acute otitis media by three years of age. Non-typable strains of *Haemophilus influenzae* account for 25–30% of all cases of otitis media, 53% of recurrent otitis media, and are the primary pathogens isolated from 62% of cases of chronic otitis media with effusion. Although non-typable *Haemophilus influenzae* (NTHi) are primary pathogens in otitis media, neither the pathogenic mechanisms nor the host immunological response has been fully defined for this disease.

Fimbriae, which are surface appendages found on non-typable *Haemophilus influenzae*, are produced by 100% of the bacteria recovered from the middle ears and nasopharyngeal region of children with chronic otitis media. A vaccine comprised of fimbrin, a filamentous protein derived from the fimbriae of non-typable *Haemophilus influenzae* was previously developed and is useful in studying, preventing, or reducing the severity of otitis media. However, existing methodologies to isolate fimbrin protein from the bacterial outer membrane are tedious and time-consuming. Similarly, purification of fimbrin expressed by the fimbrin gene in other host vector, is also tedious due to the homology between the fimbrin protein and the outer membrane proteins of the host vector.

A strategy with other bacterial species has been to use an alternative immunogen having relatively short linear peptides. However, such alternative immunogens are of limited value since antibodies to such alternative immunogens frequently fail to recognize the native pathogen.

It would be desirable to have an immunogenic composition to immunize animals against non-typable *Haemophilus influenzae* which does not depend on tedious purification techniques.

SUMMARY OF THE INVENTION

The present invention provides synthetic chimeric fimbrin peptides which induce an immunogenic response in animals to non-typable *Haemophilus influenzae* and that do not require tedious purification techniques. The synthetic chimeric fimbrin peptides are synthesized using commercially available peptide synthesizers. Preferably the synthetic chimeric fimbrin peptides are from about 18 to about 55, more preferably from about 35 to about 45, most preferably about 40–41 amino acids. The synthetic chimeric fimbrin peptides comprises three peptide units. The first peptide unit preferably contains 12 to 35, more preferably 15 to 30, most preferably 18 to 19 amino acids and is a subunit of the fimbrin protein. Preferably, the fimbrin subunit is comprised of the amino acids of Sequence ID No. 1 or Sequence ID No. 2. The amino acid of Sequence ID No. 1 is:

The amino acid of Sequence ID No. 1 is:

Arg-Ser-Asp-Tyr-Lys-Phe-Tyr-Glu-Asp-     SEQ ID NO: 1
Ala-Asn-Gly-Thr-Arg-Asp-His-Lys-Lys

The amino acid of Sequence ID No. 2 is:

Tyr-Gln-Trp-Leu-Thr-Arg-Val-Gly-Lys-     SEQ ID NO: 2
Tyr-Arg-Pro-Gln-Asp-Lys-Pro-Asn-Thr

The second peptide unit is a t cell epitope and preferably has from about 14 to about 22, more preferably about 15 to 21, most preferably 16 amino acids. The second peptide unit preferably has the following amino acid sequence:

Leu-Ser-Leu-Ile-Lys-Gly-Val-Ile-Val-     SEQ ID NO: 3
His-Arg-Leu-Glu-Gly-Val-Glu

The third peptide unit is a linker peptide unit which joins the first and second peptide unit. The linking sequence preferably has from about 2 to about 15 amino acids, more preferably from about 2 to about 10 amino acids, most preferably from about 5 to about 6 amino acids. The most preferred amino acid sequence for the linker peptide unit is shown in sequence ID NO. 4. The amino acid of Sequence ID NO. 4 is:
Gly-Pro-Ser-Leu-Lys-Leu SEQ ID NO. 4

The synthetic chimeric fimbrin peptides are useful immunogens against NTHi and also useful as laboratory tools for detecting antibodies in sera. The invention also relates to an immunogenic composition containing the synthetic chimeric fimbrin peptides and a pharmacologically acceptable carrier.

DETAILED DESCRIPTION OF THE INVENTION

Figure 1:
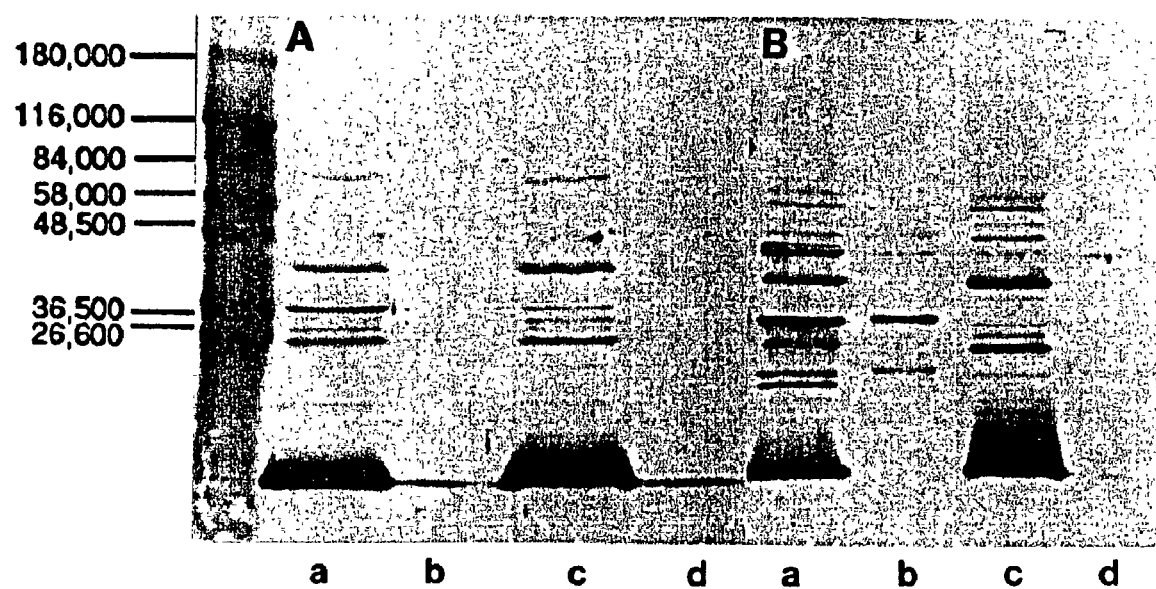
FIG. 1A is a western blot of sera obtained from a rabbit before immunization with LB1.sub.IFA. Lane a contains a mixture of sera and enriched outer membrane protein preparation from NTHi #1128. Lane b contains a mixture of sera and NTHi #1128 isolated fimbrin protein (25 and 37 kDa species). Lane c contains a mixture of sera and an enriched outer membrane protein (OMP) preparation of non-fimbriated mutant of NTHi. Lane d contains a mixture of sera and a 26 kDa outer membrane protein e of a non-fimbriated mutant, which is not fimbrin. The stained material in Lanes b and d which appears at ~48 kDa is an artifact originating in the solubilizing buffer. The unmarked lane contains prestained molecular mass standards.
FIG. 1B is a western blot of anti-LB1.sub.IFA antisera obtained from rabbit after immunization. Lane a contains a mixture of sera and enriched outer membrane protein preparation from NTHi #1128. Lane b contains a mixture of sera and NTHi #1128 isolated fimbrin protein (25 and 37 kDa species). Lane c contains a mixture of sera and an enriched outer membrane protein preparation of a non-fimbriated mutant. Lane d contains a mixture of sera and a 26 kDa outer membrane protein e of non-fimbriated mutant which is not fimbrin. The stained material in Lanes b and d which appears at ~48 kDa is an artefact originating in the solubilizing buffer. The unmarked lane contains prestained molecular mass standards.

The present invention provides synthetic chimeric fimbrin peptides which induce an immunogenic response in animals to non-typable *Haemophilus influenzae* and that do not require tedious purification techniques. The synthetic chimeric fimbrin peptides reduce the severity of otitis media caused by *Haemophilus influenzae*. The synthetic chimeric fimbrin peptides are synthesized using commercially available peptide synthesizers.

The synthetic chimeric fimbrin peptides are preferably from about 18 to about 55, more preferably from about 35 to about 45, most preferably about 40–41 amino acids.

The synthetic chimeric fimbrin peptides comprises three peptide units. The first peptide unit preferably contains 12 to 35, more preferably 15 to 30, most preferably 18 to 19, amino acids, and is a subunit of the fimbrin protein. Preferably, the fimbrin subunit is comprised of the amino acids of Sequence ID No. 1 or Sequence ID No. 2. The amino acid of Sequence ID No. 1 is:

Arg-Ser-Asp-Tyr-Lys-Phe-Tyr-Glu-Asp-    SEQ ID NO. 1
Ala-Asn-Gly-Thr-Arg-Asp-His-Lys-Lys

The amino acid of Sequence ID No. 2 is:
Tyr-Gln-Trp-Leu-Thr-Arg-Val-Gly-Lys-    SEQ ID NO. 2
Tyr-Arg-Pro-Gln-Asp-Lys-Pro-Asn-Thr The second peptide unit is a t cell epitope and preferably has from about 14 to about 22, more preferably about 15 to 21, most preferably 16 amino acids. The second peptide unit preferably has the following amino acid sequence:

Leu-Ser-Leu-Ile-Lys-Gly-Val-Ile-Val-    SEQ ID NO. 3
His-Arg-Leu-Glu-Gly-Val-Glu

Other suitable t cell epitopes include for example the following sequences:

N-S-V-D-D-A-L-I-N-S-T-I-Y-S-Y-F-P-S-V    SEQ ID NO: 5
P-G-I-N-G-K-A-I-H-L-V-N-N-Q-S-S-E        SEQ ID NO: 6
Q-Y-I-K-A-N-S-K-F-I-G-I-T-E-L            SEQ ID NO: 7
F-N-N-F-T-V-S-F-W-L-R-V-P-K-V-S-A-S-H-L-E SEQ ID NO: 8
F-F-L-L-T-R-I-L-T-I-P-Q-S-L-N            SEQ ID NO: 9
T-C-G-V-G-V-R-V-R-S-R-V-N-A-A-N-K-K-P-E  SEQ ID NO: 12

The third peptide unit is a linker peptide unit which joins the first and second peptide unit. The linking sequence preferably has from about 2 to about 15 amino acids, more preferably from about 2 to about 10 amino acids, most preferably from about 5 to about 6 amino acids. The most preferred amino acid sequences for the linker peptide unit is shown in sequence ID NO. 4. The amino acid of Sequence ID No. 4 is:
Gly-Pro-Ser-Leu-Lys-Leu SEQ ID NO. 4

Immunizing animals with synthetic chimeric fimbrin peptides induces an immune response to the fimbrin protein and reduces the concentration of NTHi in animals. The two preferred synthetic chimeric fimbrin peptides are immunogenic in-vivo and antisera generated against them were immunoreactive against both denatured and native fimbriae.

The synthetic chimeric fimbrin peptides are more desirable than immunogens isolated from bacteria because the synthetic chimeric proteins are pure and easy to synthesize.

The Preferred Synthetic Chimeric Fimbrin Peptides

The synthetic chimeric fimbrin peptide LB1, also referred to herein as "LB1", is a 40 mer peptide which comprises a 19-mer subunit derived from fimbrin representing the Arg117 to Gly135 region, joined to MVF peptide via a 5 or 6 residue linker. The MVF is a 15 amino acid sequence from a T-cell epitope used is derived from MVF Seq. 208–302 the fusion protein of measles virus. The LB1 amino acid sequence is shown below as SEQ. ID. NO. 10:

H₂N-Arg-Ser-Asp-Tyr-Lys-Phe-Tyr-Glu-       SEQ ID. NO. 10

Asp-Ala-Asn-Gly-Thr-Arg-Asp-His-Lys-

Lys-Gly-Pro-Ser-Leu-Lys-Leu-<u>Leu-Ser-</u>

<u>Leu-Ile-Lys-Gly-Val-lle-Val-His-Arg-</u>

<u>Leu-Glu-Gly-Val</u>-Glu-COOH

The synthetic chimeric fimbrin peptide LB2, also referred to herein as "LB2", is a 40 mer peptide which comprises a 18-mer fimbrin subunit representing Tyr163 to Thr180, joined to MVF peptides via a 5 or 6 residue linker. The LB2 amino acid sequence is shown below as SEQ. ID. NO. 11:

H₂N-Tyr-Gln-Trp-Leu-Thr-Arg-Val-Gly-       SEQ ID. NO. 11

Lys-Tyr-Arg-Pro-Gln-Asp-Lys-Pro-Asn-

Thr-Gly-Pro-Ser-Leu-Lys-Leu-<u>Leu-Ser-</u>

<u>Leu-Ile-Lys-Gly-Val-lle-Val-His-Arg-</u>

<u>Leu-Glu-Gly-Val</u>-Glu-COOH

The LB1 and LB2 synthetic chimeric fimbrin peptides are soluble in water up to a concentration of about 10 mg/mL. The solubility of the LB1 and LB2 synthetic chimeric fimbrin peptides in an aqueous solution can be increased by adding dilute acetic acid.

Synthesis of the Synthetic Chimeric Fimbrin Peptides

The synthesis, purification and sequence confirmation of the synthetic chimeric fimbrin peptides were done using established conventional techniques at the Peptide and Protein Engineering Laboratory at Ohio State University, Columbus, Ohio. Briefly, all synthetic peptides were assembled semi-manually by stepwise Fmoc-tert-butyl solid-phase synthesis on a Vega 1000 coupler according to the instructions. A 4-methylbenzhydrylamine resin was used as the solid support (0.54 mmol of Cl/g) and pre-formed pentafluorophenyl esters were used as the activating species.

The LB1 and LB2 synthetic chimeric fimbrin peptides were purified by HPLC and the composition and amino acid sequence of each peptide was confirmed by both amino acid analysis and mass spectral analysis. Preferably only as much synthetic chimeric fimbrin peptide is prepared as is needed, or aliquots of synthetic chimeric fimbrin peptide are frozen using liquid nitrogen or acetone/dry ice bath, and stored at −20° C. Alternatively, the synthetic chimeric fimbrin peptide is lyophilized, stored at −20° C., and preferably desiccated.

Immunogenicity of Synthetic Chimeric Fimbrin Peptides

Two rabbits were immunized with the LB1 synthetic chimeric fimbrin peptide and two rabbits were immunized with the LB2 synthetic chimeric fimbrin peptide. Rabbits received an initial immunizing dose of 500 .mu.g of either the LB1 or LB2 in complete Freund's adjuvant. The rabbits received a second dose of 400 .mu.g of the synthetic chimeric fimbrin peptide 21 days later. The rabbits received a third dose of synthetic chimeric fimbrin peptide in complete Freund's adjuvant 42 days later with 400 .mu.g of the same peptide in either incomplete Freund's adjuvant (IFA) or phosphate buffered saline (PBS) (one rabbit per diluent). Sera was obtained 3 weeks after each dose. The sera from each animal was assessed for titer and specificity against LB1, LB2 and fimbrial protein, by both ELISA and Western blot. The titer results are shown in Table 1.

TABLE I

RABBIT TITERS INDUCED BY SYNTHETIC Chimeric FIMBRIN PEPTIDES VERSUS SYNTHETIC PEPTIDES AND FIMBRIAL PROTEIN

| Antigen | Host species | Reciprocal Titer of Sera against: | | |
|---|---|---|---|---|
| | | LB1 | LB2 | NTHi #1128 fimbrial protein |
| LB1_IFA | Rabbit | 200,000 | 10,000 | 10,000 |
| LB1_PBS | Rabbit | 100,000 | 5,000 | 50,000 |
| LB2_IFA | Rabbit | 50,000 | 100,000 | 10,000 |
| LB2_PBS | Rabbit | 50,000 | 100,000 | 1,000 |

*Pre-immunization sera titers for all animals against each of the listed antigens was less than about 1:100.

As shown in Table I, significant titers against the synthetic chimeric fimbrin peptide immunogen were obtained with all antisera. Three of the four antisera also recognized isolated, reassembled, homologous fimbrial protein from NTHi at a titer≧1:10,000. Titers against the heterologous synthetic chimeric fimbrin peptide were also obtained. Antisera from animals immunized with LB1 produced titers against LB2 and antisera from animals immunized with LB2 produced titers against LB1. Such results perhaps reflect the antisera recognition of the MVF peptide portion of the synthetic chimeric fimbrin peptide.

FIG. 1B depicts the Western Blot of sera obtained from rabbits immunized with LB1; lane b contains a mixture of fimbrin protein isolated from NTH1 strain #1128. LB1 boosted with IFA shown in FIG. 1A, indicated the antisera recognized fimbrin in both its fully and partially denatured forms which have an approximate molecular weight of 37 and 25 kDa respectively. There was no equivalent reactivity with the control of non-fimbriated isogeneic mutant of strain #1128.

Both naive sera, that is sera from non-immunized and sera from immunized rabbits, recognized several outer membrane proteins as shown in FIGS. 1A and 1B, lanes a and c. However, sera reactivity to fimbrin (both molecular weight species) occured only after immunization with the synthetic chimeric peptide LB1 as can be seen by comparing lanes a and b of FIG. 1B with lanes a and b of FIG. 1A. Sera obtained after immunization with the synthetic chimeric fimbrin proteins does not react with equivalent bands in the nonfimbriated mutant, as shown in FIG. 1B, Lane c, nor does such sera react with outer membrane proteins from a non-fimbriated mutant which migrates similarly (26 kDa) but is not fimbrin as shown in FIG. 1B, lane d. Similar results were obtained from LB1 boosted with phosphate buffered saline.

The western blot of sera collected from rabbits immunized with LB2, not shown, also had similar results.

Four chinchillas were immunized with the LB1 synthetic chimeric fimbrin peptide and four chinchillas were immunized with the LB2 synthetic chimeric fimbrin peptide. Chinchillas received an initial immunizing dose of 100 μg of either the LB1 or LB2 in complete Freund's adjuvant. The chinchillas received a second dose of 50 μg of either the LB1 or LB2 in incomplete Freund's adjuvant 30 days later. Sera was obtained 2 weeks after the second dose. The sera from each animal was assessed for titer and specificity against LB1, LB2 and fimbrial protein, by both ELISA and Western blot. The titer results are shown in Table II.

TABLE II

| Antigen | Host species | Reciprocal Titer* of Sera against | | |
|---|---|---|---|---|
| | | LB1 | LB2 | NTHi #1128 fimbrial protein |
| LB1$_{IFA}$ | Chinchilla | 50,000 | 5,000 | 15,000 |
| LB2$_{IFA}$ | Chinchilla | 1,000 | 50,000 | 10,000 |

*Pre-immunization sera titers for all animals against each of the listed antigens was less than about 1:100.
IFA—incomplete Freund's adjuvant.

As shown in Table II, high titered anti-synthetic chimeric fimbrin peptide antisera were again obtained, with LB1 being somewhat more immunogenic than LB2 in the chinchilla. Both sera also reacted with isolated reassembled fimbrial protein; sera from animals immunized with LB1 had at a reciprocal titer of 15,000 to the fimbrin protein, sera from animals immunized with LB2 had reciprocal titer of 10,000.

Western blot reactivity with chinchilla antisera was the same as obtained with the rabbit antisera as described above, as shown in FIGS. 2A, 2B and 2C.

Figure 2:
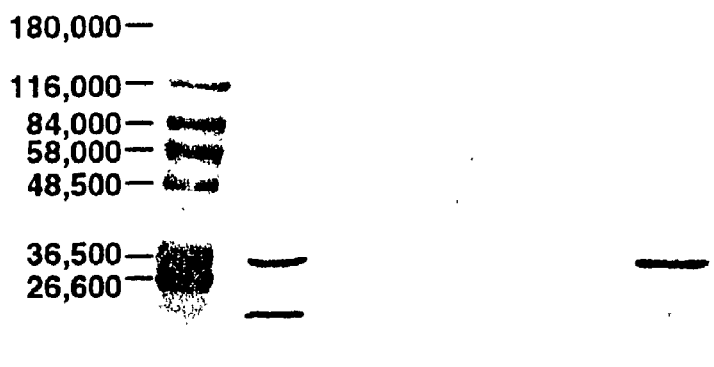
FIG. 2A is a western immunoblot of chinchilla anti-LB1 antisera. Lane a contains a mixture of sera and NTHi #1128 enriched OMP preparation. Lane b contains a mixture of sera and isolated fimbrin from NTHi #1128. Lane c contains a mixture of sera and LB1. Lane d contains a mixture of sera and LB2. Lane e contains a mixture of sera and NTHi #86-028NP enriched OMP preparation. Lane f contains a mixture of sera and isolated fimbrin from NTHi #86-028NP. The lane marked "Std" contains pre-stained molecular mass markers; mass in kDa is given along left side of immunoblot.
FIG. 2B is a western immunoblot of chinchilla anti-LB2 antisera. Lane a contains a mixture of sera and NTHi #1128 enriched OMP preparation. Lane b contains a mixture of sera and isolated fimbrin from NTHi #1128. Lane c contains a mixture of sera and LB1. Lane d contains a mixture of sera and LB2. Lane e contains a mixture of sera and NTHi #86-028NP enriched OMP preparation. Lane f contains a mixture of sera and isolated fimbrin from NTHi #86-028NP. The lane marked "Std" contains pre-stained molecular mass markers; mass in kDa is given along left side of immunoblot.
FIG. 2C is a western immunoblot of chinchilla anti-fimbrial protein antisera. Lane a contains a mixture of sera and NTHi #1128 enriched OMP preparation. Lane b contains a mixture of sera and isolated fimbrin from NTHi #1128. Lane c contains a mixture of sera and LB1. Lane d contains a mixture of sera and LB2. Lane e contains a mixture of sera and NTHi #86-028NP enriched OMP preparation. Lane f contains a mixture of sera and isolated fimbrin from NTHi #86-028NP. The lane marked "Std" contains pre-stained molecular mass markers; mass in kDa is given along left side of immunoblot.
Figure 2:
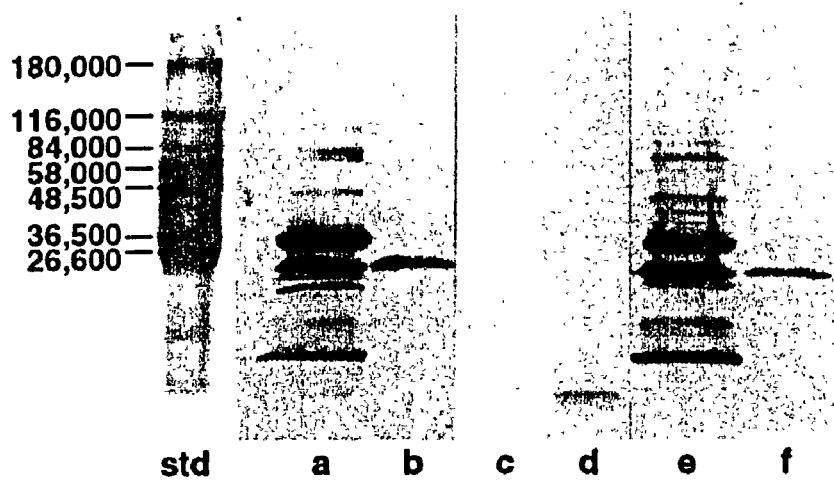
Figure 2:
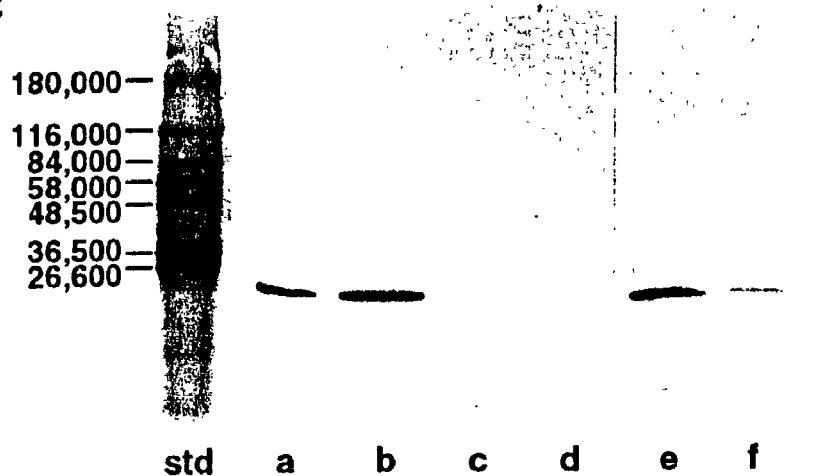

As can be seen in FIG. 2A, lane c the anti-LB1 only recognized the LB1. As seen in FIG. 2B, the anti-LB2 recognized itself, as shown in lane d, and also recognized homologous fimbrin, either contained in the outer membrane preparation, shown in lane a, or as isolated fimbrin, as shown in lane b. In addition, the anti-LB2 recognized heterologous fimbrin contained in the outer membrane preparation, lane e. As seen in FIG. 2, the anti-fimbrin recognizes itself as shown in lanes a and b, and recognizes a heteroloous fimbrin in lanes e and f.

A second study employing 20 chinchillas was conducted in the same manner as the above chinchilla study and essentially identical results were obtained.

Ability of Anti-Peptide Antibody to Recognize Native Fimbriae

Two unfixed NTHi strain #1128 cells were indirectly immunolabeled with chinchilla anti-LB1$_{IFA}$ serum and 10 nm gold-chimeric Protein A. The preparation was subjected to stable, low-angle shadow casting with platinum and palladium to impart a sense of height to low-profile fimbriae. A transmission electron micrograph of the cells is shown in FIG. 3.

Figure 3:
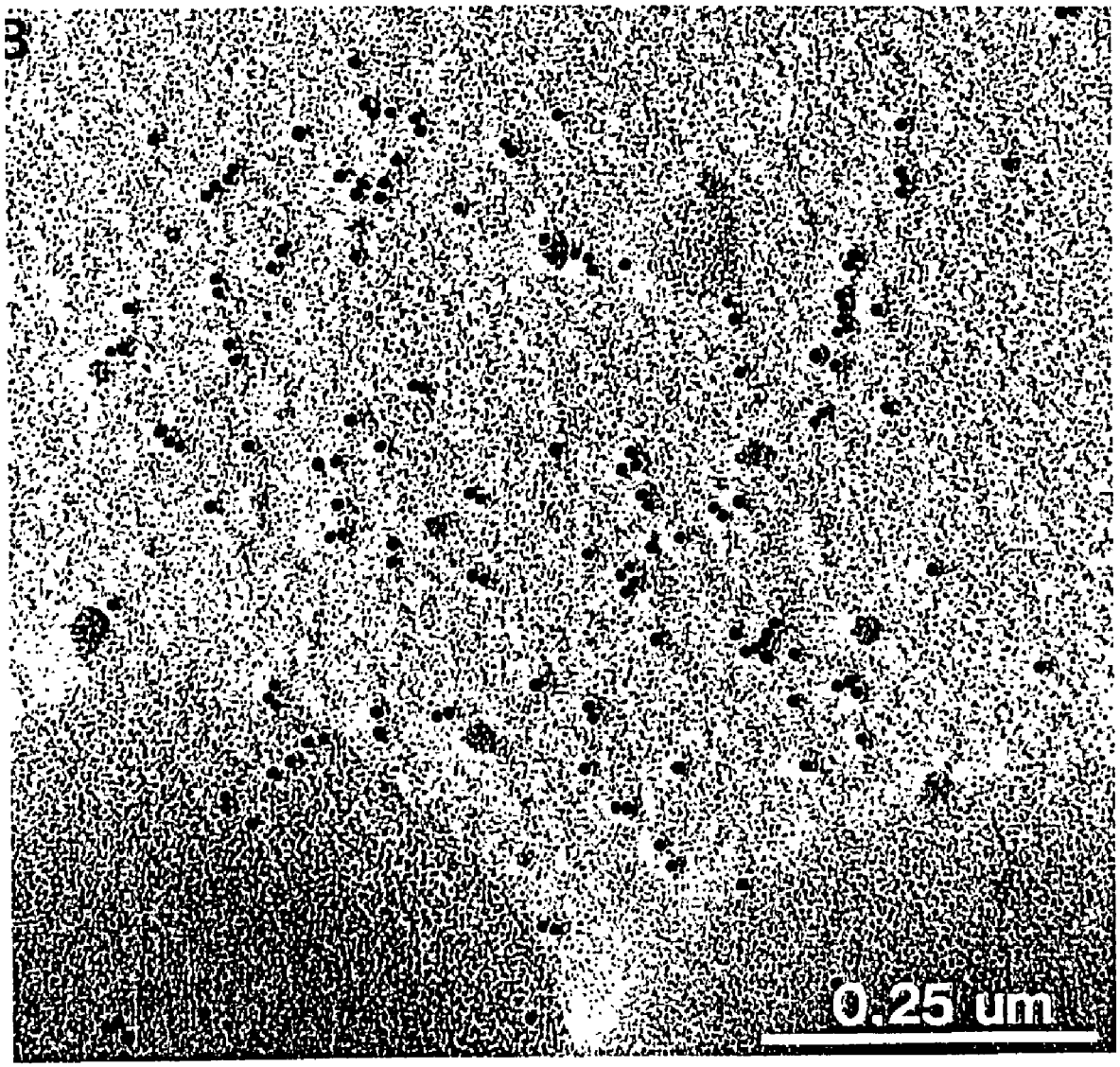
FIG. 3 is a transmission electron micrograph of two unfixed NTHi strain #1128 cells, shown at bottom of the Figure, which were indirectly immuno-labeled with chinchilla anti-LB1$_{IFA}$ serum and 10 nm gold-chimeric Protein A.

The transmission electron micrograph of the indirect immunogold labeled NTHi, shown in FIG. 3, demonstrated that chinchilla anti-LB1 IFA antiserum recognized native fimbriae of whole, unfixed NTHi strain #1128. Equivalent results were obtained with anti-serum directed against LB2.

The immunogold chimeric anti-LB1$_{IFA}$ sera is labeling a fimbriae, these are the structures which radiate outwardly from the bacterial outer membrane and is not simply labeling the outer membrane itself. The fimbrial "tracks" with associated gold spheres are visible in this shadow cast preparation of FIG. 3. This ability of the antisera to LB1 and LB2, to recognize native fimbriae is particularly significant because, historically, short linear peptides have failed as immunogens due to the inability of short peptides to mimic the secondary and tertiary structure of the targeted epitope. Thus, these other conventional short linear peptides failed to protect against other diseases because they did not generate antibodies which recognized and bind to native structures.

Anti-LB1 and anti-LB2, as demonstrated by both ELISA and the indirect immunolabeling, bind to isolated fimbrial filaments and to native fimbriae. Such binding is believed to be due, in part, to the synthetic chimeric fimbrin protein mimicking the secondary structure due to innate heptapeptide periodicity along the length of fimbrin protein. This periodicity in the fimbrin imparts a coiled-coil motif to fimbrin protein and thus an aspect of secondary character to individual peptides. The secondary character possessed by the synthetic chimeric fimbrin peptides likely contributes to the ability of the antibody created against the synthetic chimeric proteins to recognize native fimbrin protein.

Synthetic Chimeric Peptides Inhibit Adherence of NTHi to Epithelial Cells

LB1 and LB2 were each added to the lumen of excised chinchilla tracheas and incubated for about 1 hour. Next $10^8$ cFu NTHi/ml were added to the cultures and incubated for about 1 hour. The tracheas were rinsed, homogenized, diluted and plated onto chocolate agar. The NTHi colonies were then counted. The results are shown below in Table III.

TABLE III

INHIBITION OF ADHERENCE OF NTHI TO ACTIVE CILIATED TRACHEAL MUSCOSAL EPITHELIUM BY SYNTHETIC Chimeric FIMBRIN PEPTIDES

| Chimeric Synthetic Fimbrin Peptide | concentration µg/ml (n) | mean % inhibition (cfu/mm trachea) versus controls (± s.e.m.) |
|---|---|---|
| LB1 | 50 (3) | 5% (±5) |
| | 100 (4) | 65% (±10) |
| LB2 | 50 (3) | 8% (±11) |
| | 100 (4) | 11% (±19) |

As shown in Table III, synthetic chimeric fimbrin peptides, particularly LB1, had a dose-dependent effect on inhibition of adherence of NTHi strain #1128 to actively beating, ciliated chinchilla tracheal epithelium. Synthetic peptides are useful to inhibit adherence. It is believed that the inhibition is accomplished by the peptide acting as a direct stearic inhibitor of NTHi binding.

Synthetic Fimbrin Peptides as Immunogens Against Nasopharyngeal Colonization by NTHi In Vivo Nasopharyngeal colonization by NTHi was/were examined in two separate trials, study A and study B.

In study A, five cohorts of four chinchillas each were actively immunized with one of the following preparations: in complete Freund's adjuvant or a saline control preparation; 100 µg of the synthetic chimeric fimbrin peptide LB1, 100 µg of a total outer membrane protein preparation from strain #1128; 100 µg of the synthetic chimeric fimbrin peptide LB2; 10 µg isolated fimbrin protein preparation from strain #1128. The total outer membrane preparation and fimbrin were assessed for endotoxin content prior to their use as an immunogen via a chromogenic Amoebocyte Lysate assay which is commercially available from Whittaker Bioproducts under the designation QCL-1000. The preparations were subcutaneously injected into the chinchillas.

Figure 4:
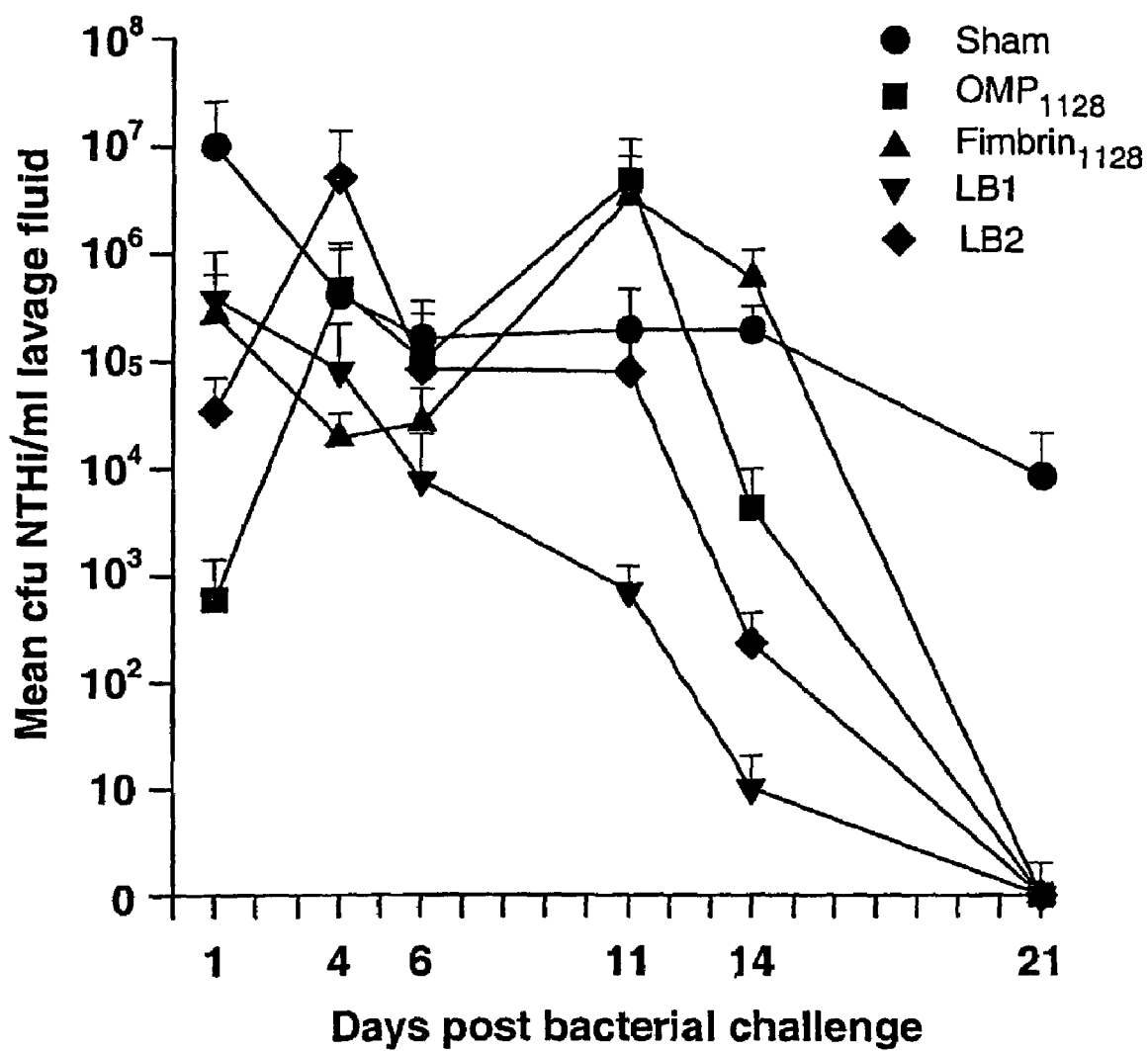
FIG. 4 is a graph showing the concentration of NTHi in nasopharyngeal lavage fluid over time in animals immunized with: LB1, depicted by inverted triangles; LB2, depicted by diamonds; outer membrane protein, depicted by squares; fimbrin, depicted by triangles and control, depicted by closed circles; which received 5×10$^8$ cfu NTHi/animal.

Then 30 days later the animals received a booster of one-half of the initial dosage of the same immunogen but in incomplete Freund's adjuvant. Ten days later they received $6\times10^6$ TCID$_{50}$ adenovirus intranasally. Thereafter, these five cohorts were divided into two groups each and challenged intranasally, about 5×10⁷ cfu of NTHi strain 1128. The chinchillas were subject to nasopharyngeal lavage over a 21 day period, and the lavage fluid was examined and quantified for NTHi. The NTHi concentration was determined by plating on selective media. The NTHi lavage fluid concentration was plotted over time. The plot is shown in FIG. 4. As can be seen from FIG. 4, immunization with LB1 and LB2 lowered the NTH1 in lavage fluid to 0 by Day 21 in contrast to the control fluid which had 10⁴ NTH1 present on Day 21.

The study was repeated in study B except that in study B, the intranasal challenge dose of NTHi #1128 was significantly higher, 1.5×10⁸ cfu/animal. Again, the NTHi lavage fluid concentration was plotted over time. The plot is shown in FIG. 5.

Figure 5:
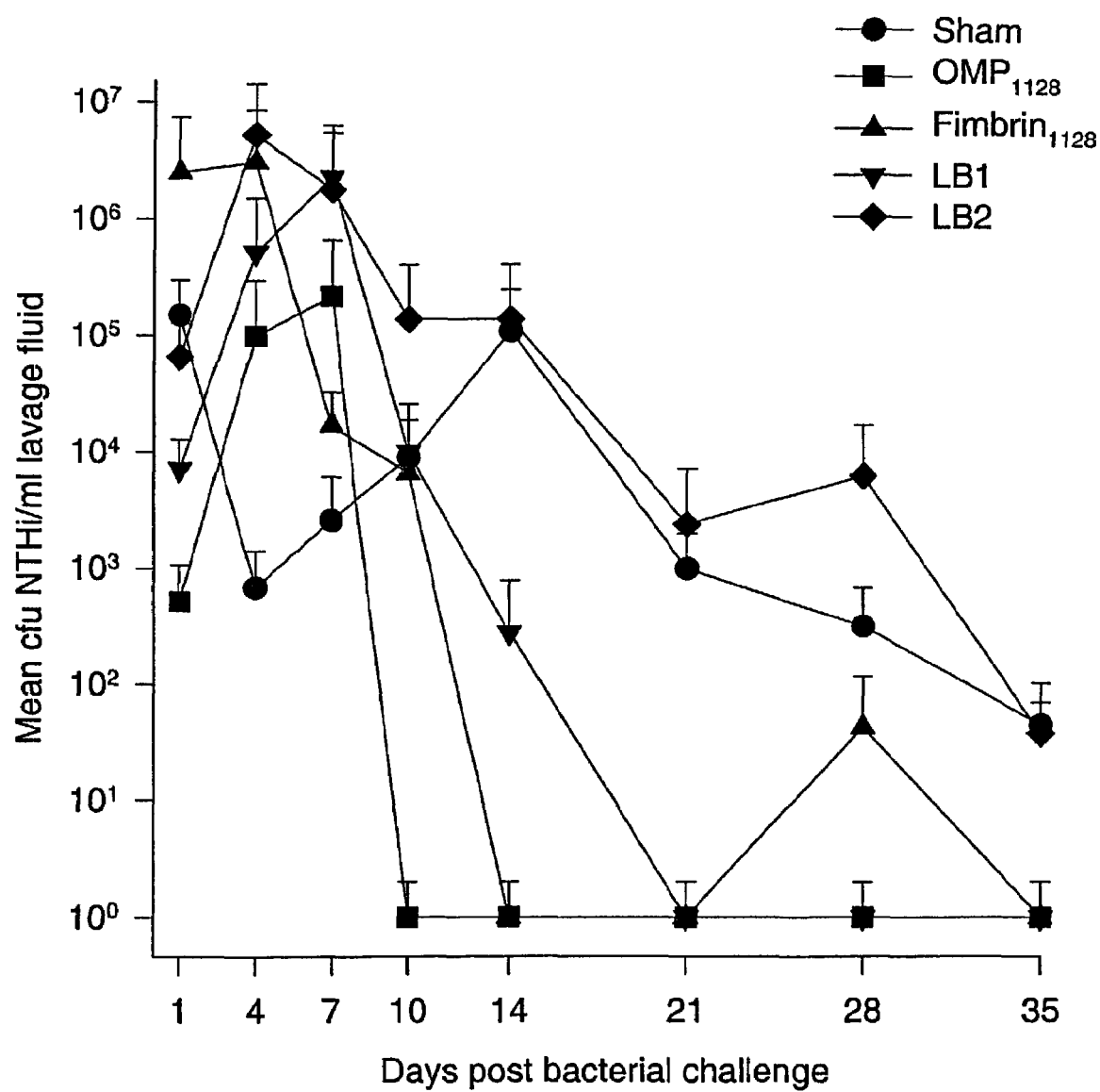
FIG. 5 is a graph showing the concentration of NTHi in nasopharyngeal lavage fluid over time in animals immunized with: LB1, depicted by inverted triangles; LB2, depicted by diamonds; outer membrane protein depicted by squares; fimbrin, depicted by triangles and control, depicted by closed circles; which received 1.5×10$^8$ cfu NTHi/animal.

As can be seen from FIG. 5, immunization with LB1 lowered the NTH1 in lavage fluid to 0 by Day 21 in contrast to the control fluid which had about 10³ NTH1 present on Day 21. The LB2 performed less well at the higher challenge dose of bacteria.

Nasopharyngeal colonization is an initial step required for the development of the disease, otitis media. Since the immunization with synthetic chimeric fimbrin peptide inhibits nasopharyngeal colonization of NTHi, the synthetic chimeric fimbrin peptides will apparently also help to inhibit the development of otitis media.

The Synthetic Chimeric Fimbrin Peptides used as a Diagnostic Tool

The synthetic chimeric fimbrin peptides are useful in laboratory assays, for example, to detect antibodies in sera to NTHi.

An anti-serum Elisa was performed by first coating an immulon 1, flat bottom plate containing 96 wells with varied concentrations of LB1 and LB2 according to the dilute checkerboard assay method. The LB1 and LB2 were diluted first in carbonate-bicarbonate buffer at pH 9.6. This coating buffer contained 1.59 g/L NaCO₃, 2.93 g/L NaHCO₃ at a pH of 9.6. 50 µl of the LB1 or LB2 were added for each well and incubated at 4° C. overnight. After the overnight incubation, the liquid was emptied from the plates and 100 µl per well of 10 mM PBS at pH 7.4 with 0.5% BSA was added, and incubated at 37° C. for 1 hour. Next, the liquid was emptied from the plate and washed three times with 10 mM PBS at pH 7.4 with 0.05% Tween 20 (PBT) at a volume of 250 µl per well. Then the plate was emptied by pounding three times onto paper towels. Next, 50 µl per well of the sera to be assayed was diluted in 10 mM PBS at a pH of 7.4 and added to the plate and incubated at 37° C. for one hour. The liquid was then emptied from the plates and washed three times with 10 mM PBS at pH 7.4 containing 0.05% Tween 20 (PBT) at a volume of 250 µl per well and the plates were pounded three times onto paper towels. Next, 500 µl per well of secondary antibody diluted 1 to 1000 times in PBT was added. Where the sera to be assayed was rabbit, the secondary antibody was HRP chimeric goat anti-rabbit antibody. Where the sera to be assayed was chinchilla sera, then the secondary antibody was HRP protein A. The secondary antibody was incubated at 37° C. for one hour. Next, the liquid was emptied from the plates and washed three times with 10 mM PBS at pH 7.4 containing 0.05% Tween 20. Next, one tablet o-phenylenediamine was suspended in 12 ml citrate phosphate buffer at pH 5.0. The citrate phosphate buffer contained 0.1 M citric acid, 1.0 M Na₂HPO₄ at pH 5.0. Next 12 µl 30% H₂O₂ was added to the o-phenylenediamine solution and 100 µl of this mixture was added to each well. The solution was incubated at room temperature in the dark and after 10 minutes, the absorbencies were read at 400 nm. The reaction was stopped at 16 minutes with 100µ per well of 2NH₂SO₄ and the plates were then read at 490 nm. Chinchilla sera was assayed according to the above method and the results are shown below in Table IV.

TABLE IV

TITERS OBTAINED USING Synthetic chimeric FIMBRIN PEPTIDES AS ANTIGEN IN ELISA USING TEST SERA

| Antigen | Sera Source | Reciprocal Titer |
| --- | --- | --- |
| Sham | Pre immune | 100 |
| Sham | immunized | 100 |
| LB1 | Pre infection | ≦100 |
| LB1 | Post infection | >500 |
| LB2 | Pre-infection | ≦100 |
| LB2 | Post-infection | 500 |

As shown in Table IV, both the LB1 and LB2 synthetic chimeric peptides are useful to detect antibodies in sera directed to NTHi.

While the immunogenic composition containing the synthetic chimeric fimbrin peptide has been administered in a carrier such as Freund's adjuvant, PBS and incomplete Freund's adjuvant, other carriers, including pharmacologically acceptable carriers, are also suitable.

Thus synthetic chimeric fimbrin peptides are also administered to prevent or reduce adherence of NTHi to host cells thereby preventing or reducing the severity of otitis media. The synthetic chimeric fimbrin peptide is administered, before or after infection with NHTi, such as by an intranasal spray comprising the synthetic chimeric fimbrin peptide and a carrier.

Although certain embodiments of this invention have been shown and described, various adaptations and modifications can be made without departing from the scope of the invention as defined in the appended claims. For example, peptides or portions thereof having substantially the same amino acid sequence as described herein, particularly those amino acids as shown in SEQ ID NO 1, SEQ ID NO 2, SEQ ID NO 11, SEQ ID NO 12, are within the scope of the invention.

What is claimed is:

1. A method for inducing an immune response in a mammal against non-typable strains of *Haemophilus influenzae* comprising the step of administering an immunogenic composition comprising a carrier and a synthetic chimeric fimbrin peptide which contains a fimbrin subunit peptide sequence from 12 to 18 amino acids in length, said fimbrin subunit peptide sequence comprising, respectively, from 12 to 18 consecutive amino acids set forth in SEQ. ID. NO. 1.

2. The method of claim 1, wherein the synthetic chimeric fimbrin peptide has the amino acid sequence of SEQ. ID NO. 10.

3. The method of claim 1, wherein the fimbrin subunit peptide sequence is 18 amino acids in length and consists of the amino acid sequence set forth in SEQ. ID. No. 1.

4. A method for inducing an immune response in a mammal against non-typable strains of *Haemophilus influenzae* comprising the step of administering an immunogenic composition comprising a carrier and a synthetic chimeric fimbrin peptide, said synthetic chimeric fimbrin peptide comprising:

a. a first peptide unit of 12 to 18 amino acids in length and having, respectively, from 12 to 18 consecutive amino acids set forth in SEQ. ID. NO. 1;
b. a second peptide unit comprising a t cell epitope; and
c. a third linker peptide unit which connects the first peptide unit to the second peptide unit.

5. The method of claim 4, wherein the first peptide unit is 18 amino acids in length and consists of the amino acid sequence set forth in SEQ. ID NO: 1.

6. The method of claim 4, wherein the synthetic chimeric fimbrin peptide comprises the amino acid sequence of SEQ. ID. NO: 10.

7. The method of claim 4, wherein the second peptide unit comprises an amino acid sequence selected from the group consisting of: SEQ. ID. NO: 3; SEQ. ID. NO: 5; SEQ. ID. NO: 6; SEQ. ID. NO: 7; SEQ. ID NO: 8; SEQ. ID. NO: 9; and SEQ. ID NO: 12.

8. The method of claim 4, wherein the third linker peptide unit has from about 2 to about 15 amino acids and comprises from 2 to 6 amino acids set forth in SEQ. ID. No. 4.

* * * * *